United States Patent
Pfeiffer

(10) Patent No.: US 10,656,137 B2
(45) Date of Patent: May 19, 2020

(54) METHOD FOR PRODUCING A NANO-GAP IN A BRITTLE FILM ASSISTED BY A STABILIZING SUBSTRATE

(71) Applicant: Ethan Pfeiffer, New Braunfels, TX (US)

(72) Inventor: Ethan Pfeiffer, New Braunfels, TX (US)

(*) Notice: Subject to any disclaimer, the term of this patent is extended or adjusted under 35 U.S.C. 154(b) by 0 days.

(21) Appl. No.: 14/860,599

(22) Filed: Sep. 21, 2015

(65) Prior Publication Data

US 2017/0082598 A1    Mar. 23, 2017

(51) Int. Cl.
| G01N 33/487 | (2006.01) |
| G01N 27/414 | (2006.01) |
| B82Y 40/00  | (2011.01) |

(52) U.S. Cl.
CPC ........ *G01N 33/48721* (2013.01); *B82Y 40/00* (2013.01); *Y10S 977/788* (2013.01); *Y10S 977/881* (2013.01); *Y10S 977/92* (2013.01)

(58) Field of Classification Search
CPC .............. G01N 33/48721; B82Y 40/00; Y10S 977/788; Y10S 977/881; Y10S 977/92
See application file for complete search history.

(56) References Cited

U.S. PATENT DOCUMENTS

| 6,132,814 A * | 10/2000 | Livesay ............. H01L 21/3105 257/E21.241 |
| 2009/0034215 A1* | 2/2009 | Wieglus ............. H01L 21/4846 361/760 |
| 2010/0171583 A1* | 7/2010 | Iovine ................. H01C 10/106 338/211 |
| 2011/0236654 A1* | 9/2011 | Hsu ....................... A44C 27/007 428/210 |
| 2012/0181507 A1* | 7/2012 | Dimitrakopoulos ... B82Y 10/00 257/29 |
| 2013/0037410 A1* | 2/2013 | Xu ........................ B82Y 15/00 204/601 |
| 2013/0108839 A1* | 5/2013 | Arnold ................ C01B 31/0438 428/195.1 |
| 2014/0217455 A1* | 8/2014 | Honma ................ H05K 3/3421 257/99 |
| 2014/0284547 A1* | 9/2014 | Dimitrakopoulos ........................ H01L 29/0673 257/9 |
| 2014/0326954 A1* | 11/2014 | Han ..................... C12Q 1/6869 257/29 |

OTHER PUBLICATIONS

Vella, J.B., Adhihetty, I.S., Junker, K., Volinsky, A.A., "Mechanical Properties and Fracture Toughness of Organo-Silicate Glass (OSG) Low-k Dielectric Thin Films for Microelectronic Applications", 2003, Int. J. Fracture, 119/120, p. 487-499.*

(Continued)

*Primary Examiner* — Katherine A Bareford
*Assistant Examiner* — Christina D McClure
(74) *Attorney, Agent, or Firm* — Spradley PLLC; Michael Spradley

(57) ABSTRACT

This application discloses a method for developing a conductive nano-gap. The first step can comprise depositing a brittle material on a substrate. Next, a conductive graphene layer can be deposited at the surface of the brittle material. Lastly, a crack can be propagated through the brittle material and the graphene using a force, the crack a nano-gap.

19 Claims, 8 Drawing Sheets

(56) References Cited

OTHER PUBLICATIONS

Onal, C.D., Ozcan, O., Sitti, M., "Atomic-Force-Microscopy-Based Nanomanipulation Systems", 2011, p. 42-1-42-15.*
Ferrari, "Raman Spectrum of Graphene and Graphene Layers", 2006, Phys Rev Lett, 97, p. 187401-1-187401-4.*
CeramTec, "Non-oxide Carmics—Silicon Carbide (SiSiC/SSiC)", 2016, p. 1-2.*

* cited by examiner

METHOD FOR PRODUCING A NANO-GAP IN A BRITTLE FILM ASSISTED BY A STABILIZING SUBSTRATE

BACKGROUND

This disclosure relates to a method for producing a nano-gap in a brittle film assisted by a stabilizing substrate.

DNA sequencing is a process used to determine the precise order of four nucleotide bases, which comprise a DNA strand. The information obtained from DNA sequencing is useful to various fields of biology and other sciences, forensics, medicines, agriculture, and other areas of study. One of the challenges of biotechnology is establishing the base sequence of individual molecules of DNA/RNA without PCR amplification or other modifications to the molecule, which can cause reading defects, and contaminations of samples. One known method of DNA sequencing is the conventional Sanger method. This method uses shotgun sequencing that only give portions of the DNA strand and can require many sequencing steps, overlapping reads, and good amount of computational power to merge the sequences. This method can be time consuming and resource intensive, thus can be costly. An alternative method for conventional Sanger method is nano-gap based (nano-pore based) sequencing. In this method, DNA can be passed through a nano-gap. DNA or RNA molecule can be electrophoretically driven in a strict linear sequence through the nano-gap whose width can approximately be a minimum of 1.5 nanometers. The molecule can be detected when the DNA molecules release an ionic current while moving through the nano-gap. Further, the amount of current is very sensitive to the size and shape of the nano-gap. If single nucleotides (bases), strands of DNA or other molecules pass through or is near the nano-gap, a characteristic change in the magnitude of the current is created through the nano-gap. Analyzing the transverse conductance (current) with respect to time the molecules composition can be extrapolated and sequenced. Using nano-gap-based sequencing a large read length and high throughput can be achieved simultaneously. However making nano-electrodes that are aligned with the nano-gap is difficult.

As such it would be useful to have a method for producing a nano-gap in a brittle film assisted by stabilizing substrate.

SUMMARY

This application discloses a method for developing a conductive nano-gap. The first step can comprise depositing a brittle material on a substrate. Next, a conductive graphene layer can be deposited at the surface of the brittle material. Lastly, a crack can be propagated through the brittle material and the graphene using a force, the crack a nano-gap.

DETAILED DESCRIPTION

Described herein is a system and method for producing a nano-gap in a brittle film assisted by a stabilizing substrate. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
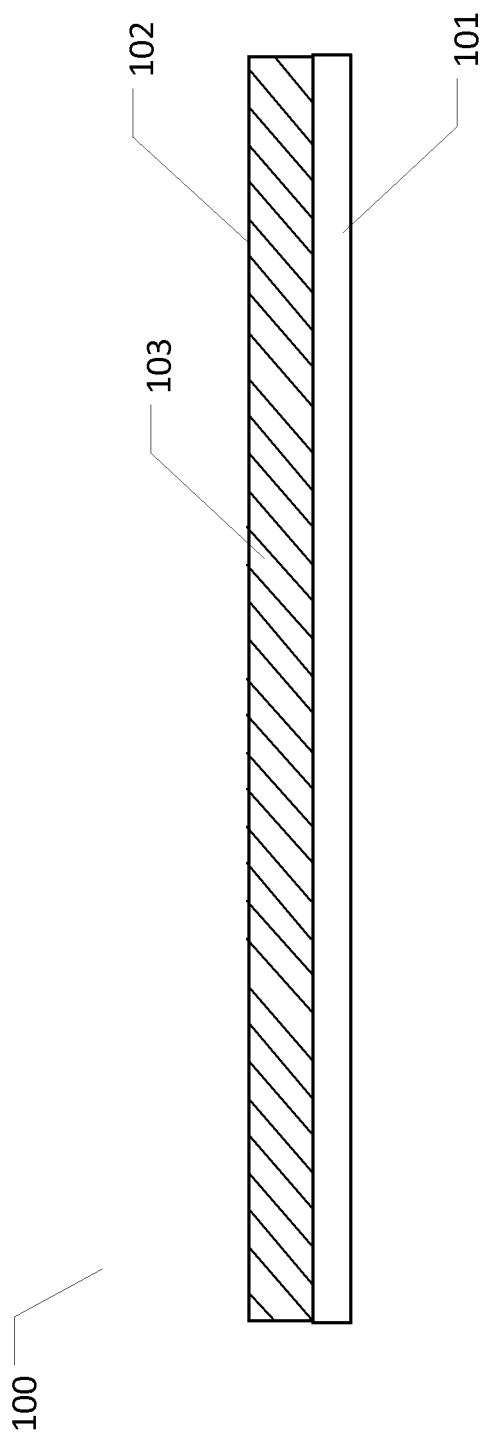
FIG. 1 illustrates a side view of a strip comprising a substrate coated with a brittle film.

FIG. 1 illustrates a side view of a strip 100 comprising a substrate 101 coated with a brittle film 102. In one embodiment, substrate 101 can be a Poly-ethylene Terephthalate (PET) film that is used as a stabilizer for strip 100. Brittle film 102 can comprise of a brittle material 103, which can include but are not limited to salt, ceramic, or silica glass substance. An example of brittle film 102 is a Spin on Glass (SOG) liquid glass. For purposes of this disclosure, SOG is a type of glass that can be applied as a liquid and cured to form a layer of glass having characteristics similar to those of SiO2. SOG is mainly used for planarization and is a dielectric.

Brittle film 102 can be deposited onto the surface of substrate 101 through a coating method such as Mayer rod coating. After substrate 101 is coated with brittle film 102, the thickness of substrate 101 can be measured to ensure that the thickness of strip 100 is within a desired height. The measurement can be taken at a point 104 of strip 100. Point 104 can be any area within strip 100.

Figure 2:
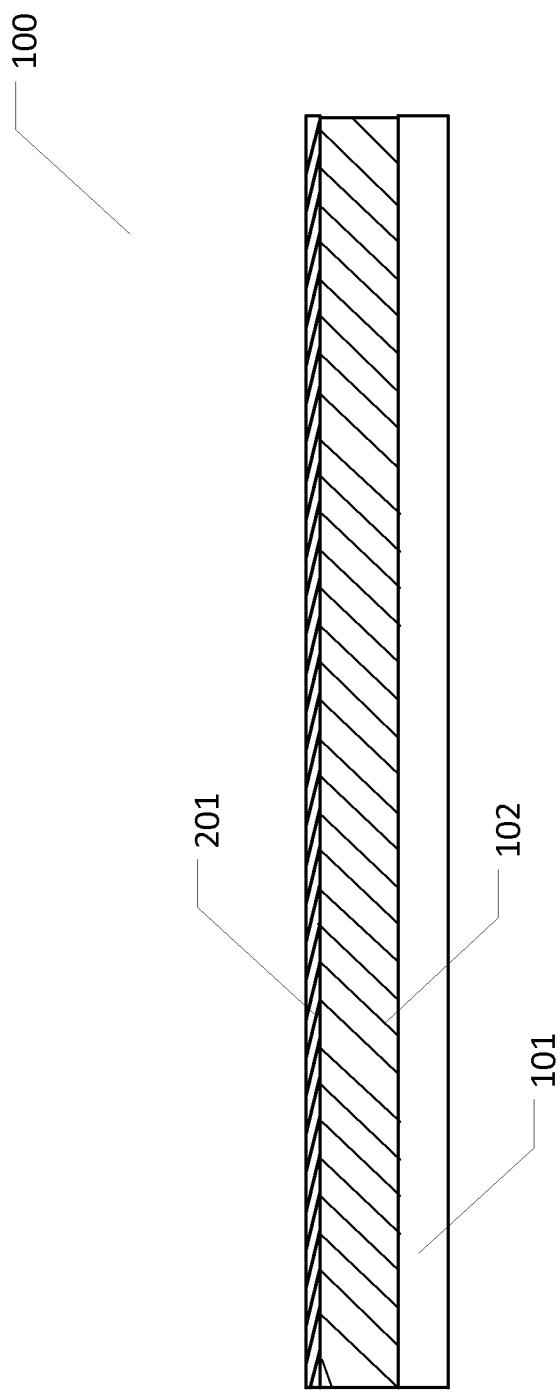
FIG. 2 illustrates a conductive two-dimensional (2D) layer deposited at the surface of a strip.

FIG. 2 illustrates a conductive two-dimensional (2D) layer 201 deposited at the surface of strip 100. In a preferred embodiment, conductive 2D layer 201 comprises graphene. For purposes of this disclosure, graphene is a 2-dimensional hexagonal carbon lattice that can survive large transmembrane pressure with intrinsic conductive properties. Therefore, graphene can be ideal for the conductive nano-gap application. After conductive 2D layer 201 is deposited onto the surface of strip 100, thickness of strip 100 can be measured again at point 104 of strip 100. Thickness of strip 100 can be measured to determine the resulting thickness after conductive 2D layer 201 is deposited. The quality of conductive 2D layer 201 can also be determined to ensure that a relevant area of conductive 2D layer 201 can still be used as a conductor. Raman spectroscopy can be used to determine the thickness (single layer, bilayer, multilayer), and quality or presence of defects on conductive 2D layer 201. After cracking, as discussed below, conductive 2D layer 201 will be divided into a first conductive 2D layer 201a and a second conductive 2D layer 201b, as shown later in FIGS. 5 and 6.

Figure 3:
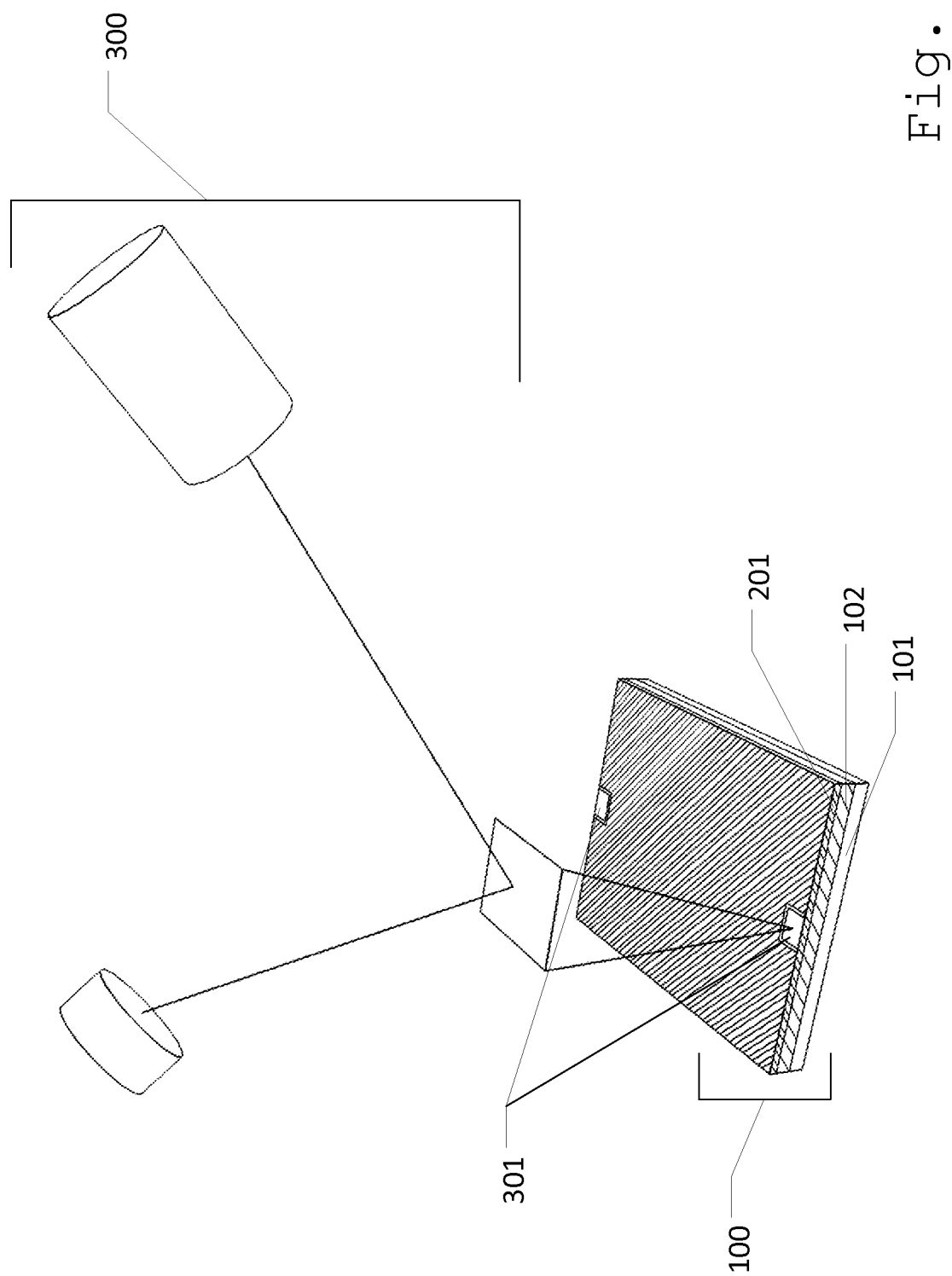
FIG. 3 illustrates a strip mounted on a microscope.

FIG. 3 illustrates strip 100 mounted onto a microscope 300. In a preferred embodiment, microscope 300 can be an atomic force microscope (AFM). In this embodiment, strip 100 can be placed within the vacuum chamber of microscope 300. Then, through an AFM scratching technique, one or more indentions 301 can be formed to mark the desired position where a crack should be formed. Such scratching can create a weak point where a crack is most likely to first form. Moreover, indentions 301 can aid microscope 300 to detect where the crack is on strip 100. Further in another embodiment, microscope 300 can be a scanning electron microscope (SEM).

Figure 4:
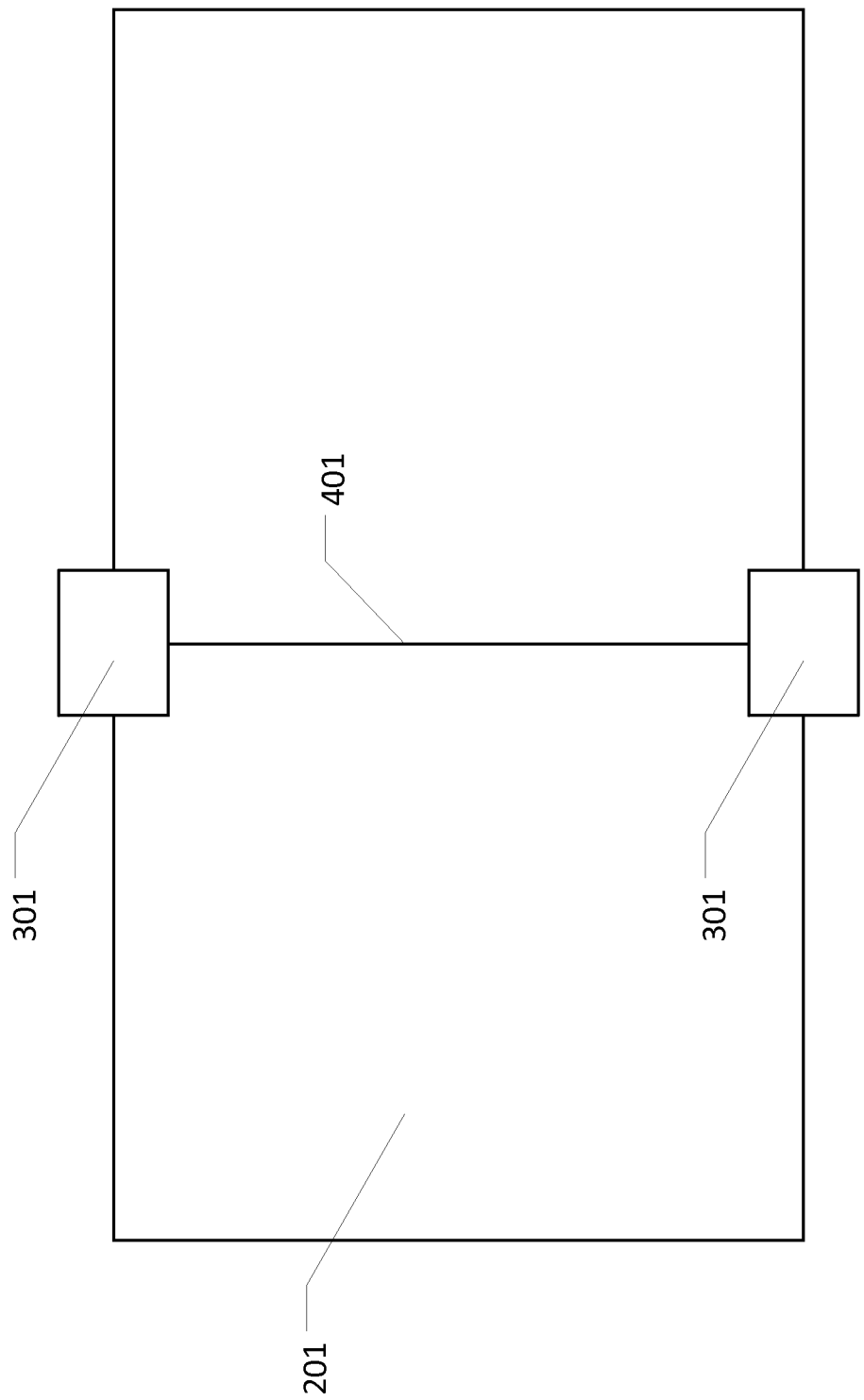
FIG. 4 illustrates a top view of a strip marked with one or more indentions.

FIG. 4 illustrates a top view of strip 100 marked with indentions 301. To produce an initial gap 401 on conductive 2D layer 201, a strain can be exerted on indentions 301. The strain in indentions 301 can produce a crack in brittle film 102 which can produce initial gap 401.

Figure 5:
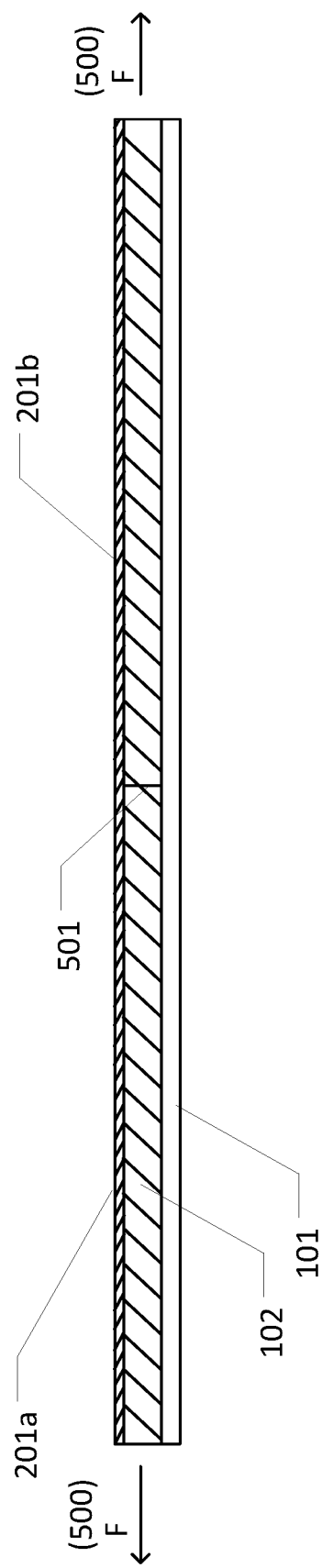
FIG. 5 illustrates propagating a crack on a strip.

FIG. 5 illustrates propagating a crack 501 on strip 100. After placing indentions 301 on strip 100, force 500 can be applied to indentions 301 to cause crack 501 in brittle film 102 and conductive 2D layer 201 to propagate. In one embodiment, force 500 can be a compression force, which exerts pressure by squeezing indentions 301. In another embodiment, force 500 can be a tensional force. In some embodiments, force 500 can be applied by bending strip 100 around a bar or a bending device. In a preferred embodiment, crack 501 can be a break created on brittle film 102 that is within indentions 301. Since brittle film 102 can have a definite feature at a nano level, when strip 100 is cracked in between indentions 301 through a controlled and supported experiment, a nano-gap 502 can be created on conductive 2D layer 201. Nano-gap 502 can be a gap within conductive 2D layer 201 that is less than 100 nanometers wide.

Figure 6:
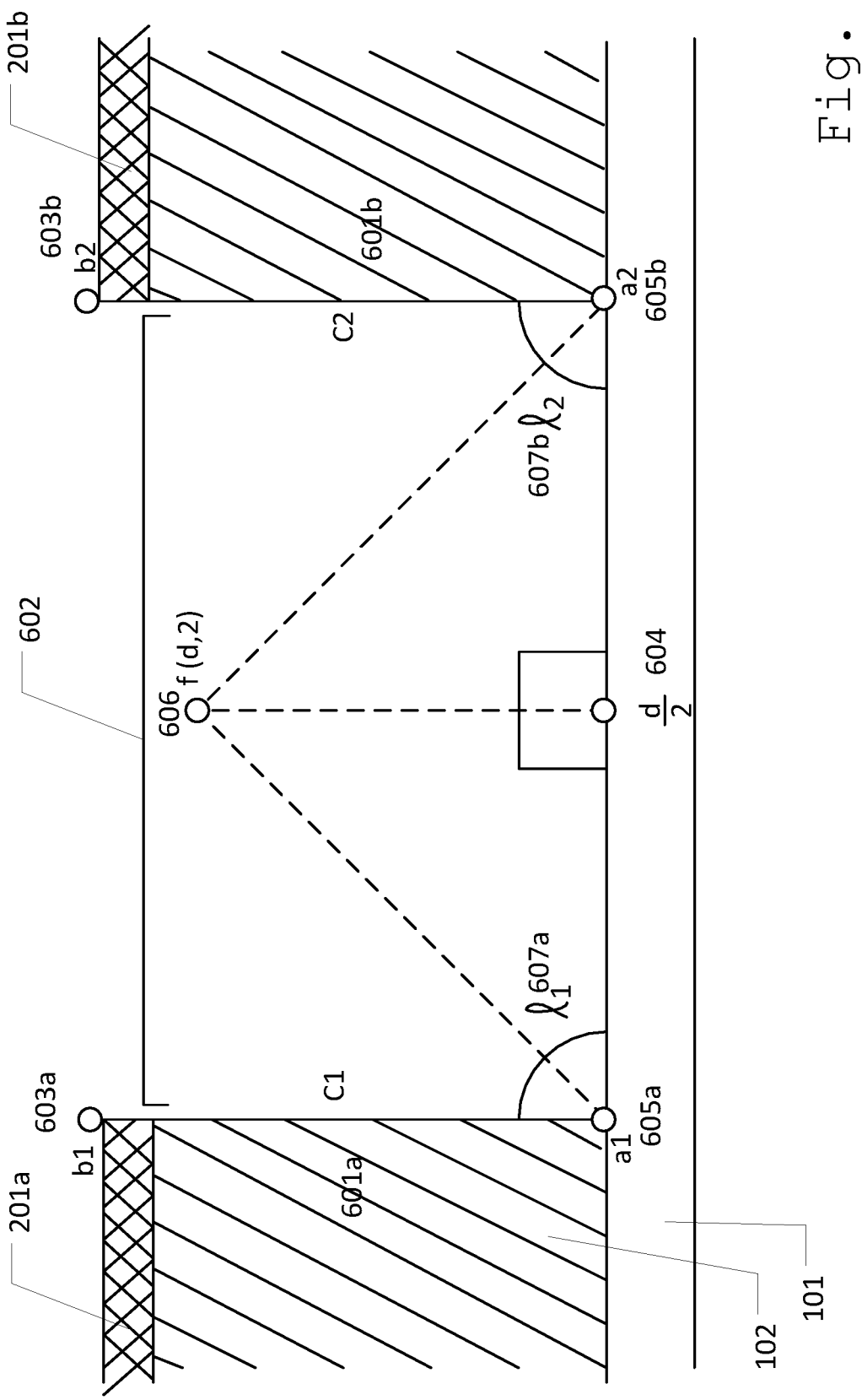
FIG. 6 illustrates exemplary measurements that can be used to calculate bending of a substrate.

FIG. 6 illustrates exemplary measurements that can be used to calculate bending of substrate 101. After the processes of propagating crack 501, nano-gap 502 can widen to as much as 400 nm. As such, substrate 101 can be bent to decrease the distance between nano-gap 502. Using known measurements on strip 100, such as a strip thickness 601, a crack width 602, and a preferred nano-gap distance, a calculation can be made to determine at what angle of bend on each side of strip 100 can be done in order to produce the preferred nano-gap distance. In one embodiment, substrate 101 can be bent using a suction method, wherein a suction cup can be placed at the bottom of strip 100, which can cause substrate 101 to bend concavely and thus a relationship between applied pressure and bend degree can be made and stabilized with further processing such as applying a "tack" similar to what is used in the art of welding by metal physical deposition methods. Strip thickness 601 can comprise brittle layer 102 and conductive 2D layer 201. Furthermore, strip thickness 601 can comprise a thickness of first-side strip 601a, a thickness of second-side strip 601b, a first-side strip height 603a, and a second-side strip height 603b. Thickness of first-side strip 601a can be the measure of thickness on one side of strip 100, while thickness of second-side strip 601b can be the measure of thickness on the other side of strip 100. Additionally, first-side strip height 603a the distance first conductive 2D layer 201a is from substrate 101, while second-side strip height 603b the distance second conductive 2D layer 201b is from substrate 101. In FIG. 6, the point at which first-side strip height 603a is measure from is marked as b1, and the point at which second-side strip height 603b is measured from is marked as b2. Crack width 602 can be the measure of the total distance between crack 501. Crack width 602 can further comprise a mid-crack distance 604, a first base point 605a, a second base point 605b, and an intersection point 606, marked as "f" on FIG. 6. Mid-crack distance 604 can be half of the total distance between crack 501. First base point 604a can be the lowest point on one side of nano-gap 502, while second base point 604b can be the lowest point on the other side of nano-gap 502. Intersection point 606 can be the common point at which first conductive 2D layer 201a and second conductive 2D layer 201b would meet as a result of a first bend 607a and second bend 607b. For purposes of this disclosure, it is assumed that movement of vertical lines on first base point 604a and second base point 604b is negligible to none at bending. The control on bending of $$\begin{pmatrix} \ell_1 \\ a_1 \end{pmatrix} \text{ and } \begin{pmatrix} \ell_2 \\ a_2 \end{pmatrix}$$

is the most important process, parameters provide an accurate way to keep first-side strip height 603a even with second-side strip height 603b.

Figure 7:
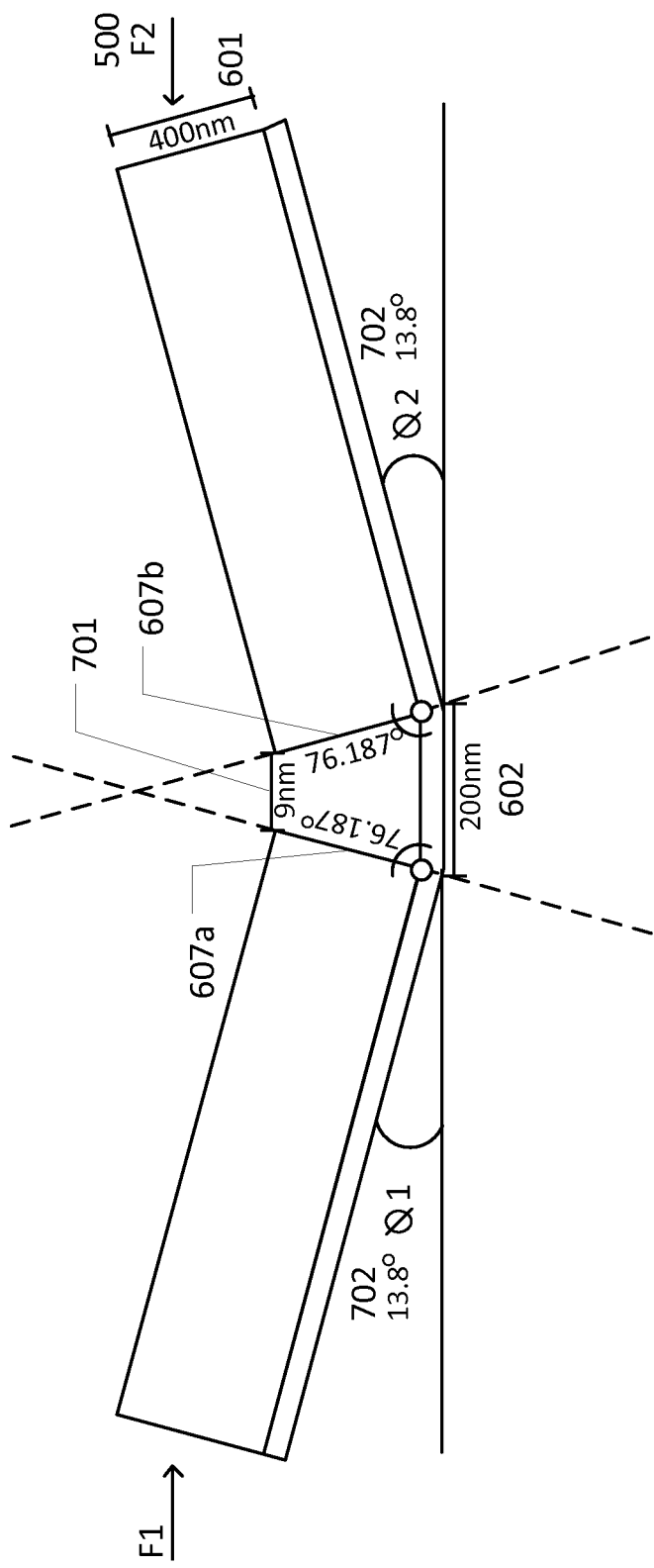
FIG. 7 illustrates an exemplary calculation of bending of a substrate.

FIG. 7 illustrates an exemplary calculation of bending of substrate 101. In example measurements shown in FIG. 7, wherein thickness of strip 601a and 601b can be at 400 nm, crack width 602 can be 200 nm, and a preferred nano-gap distance 701 can be 9 nm, an angle of bend 702 can be calculated. Preferred nano-gap distance 603 can be desired distance between nano-gap 502. Angle of bend 702 can be the required degree of angle at which either ends of substrate 101 can be bent in order to obtain preferred nano-gap distance 701. FIG. 7 illustrates substrate 101 bending at first base point 605a and second base point 605b. As each side is bent, first conductive 2D layer 201a and second conductive 2D layer 201b will move toward each other and toward intersection point 606. Further, as each side is bent, angles $l_1$ and $l_2$ decrease while $\varnothing_1$ and $\varnothing_2$ increase. A person of ordinary skill in the art will recognize that $l_1$ and $\varnothing_1$ are complementary angles and $l_2$ and $\varnothing_2$ are complementary angles. As each side is bent, first-side strip height 603a and second-side strip height 603b decrease. First-side strip height 603a can be calculated as follows using the formula $C_1 \sin(l_1) = b_{1y}$. Second-side strip height 603a can be calculated as follows using the formula $C_2 \sin(l_2) = b_{2y}$. Similarly, the distance first conductive 2D layer 201a moves horizontally toward second conductive 2D layer 201b (measured from b1) due to first bend 607a is $C_1 \cos(l_1) = b_{1x}$, and the distance second conductive 2D layer 201b moves horizontally toward first conductive 2D layer 201a (measured from b2) due to second bend 607b is $C_2 \cos(l_2) = b_{2x}$. Thus, using the given measurements in FIG. 7, crack width 602 is 200 nm. To achieve a 9 nm nanogap 502, first conductive 2D layer 201a and second conductive 2D layer 201b must each move 95.5 nm, toward each other. Using $C_1 \cos(l_1) = b_{1x}$, as 400 $\cos(l_1) = 95.5$, $l_1$ would be equal approximately 76.2 degrees. As such, angle of bend 702 ($\varnothing_1$) would be approximately 13.8 degrees.

Using the law of cosines one can determine the distance that the edge traveled as well as the resulting angle it produces in triangulation with the edge locations, a1, or b1, and a2, or b2 that may prove useful in certain applications.

To get the distance that the edge traveled on either of the sides of nano-gap 502, one can use these equation: J=

$$\sqrt{2(C1)^2 - 2(C1)^2 \cos(\phi_1)} \quad \text{or:} \quad J = \sqrt{2(C2)^2 - 2(C2)^2 \cos(\phi_1)},$$
wherein J is the distance traveled.

To get the resulting angle produced in triangulation, these equations can be used:

$$\left(\phi_1 = \cos^{-1}\left(1 - \frac{J^2}{2C1^2}\right) \quad \text{or} \quad \phi_2 = \cos^{-1}\left(\frac{J^2}{2C2^2}\right)\right)$$

Figure 8:
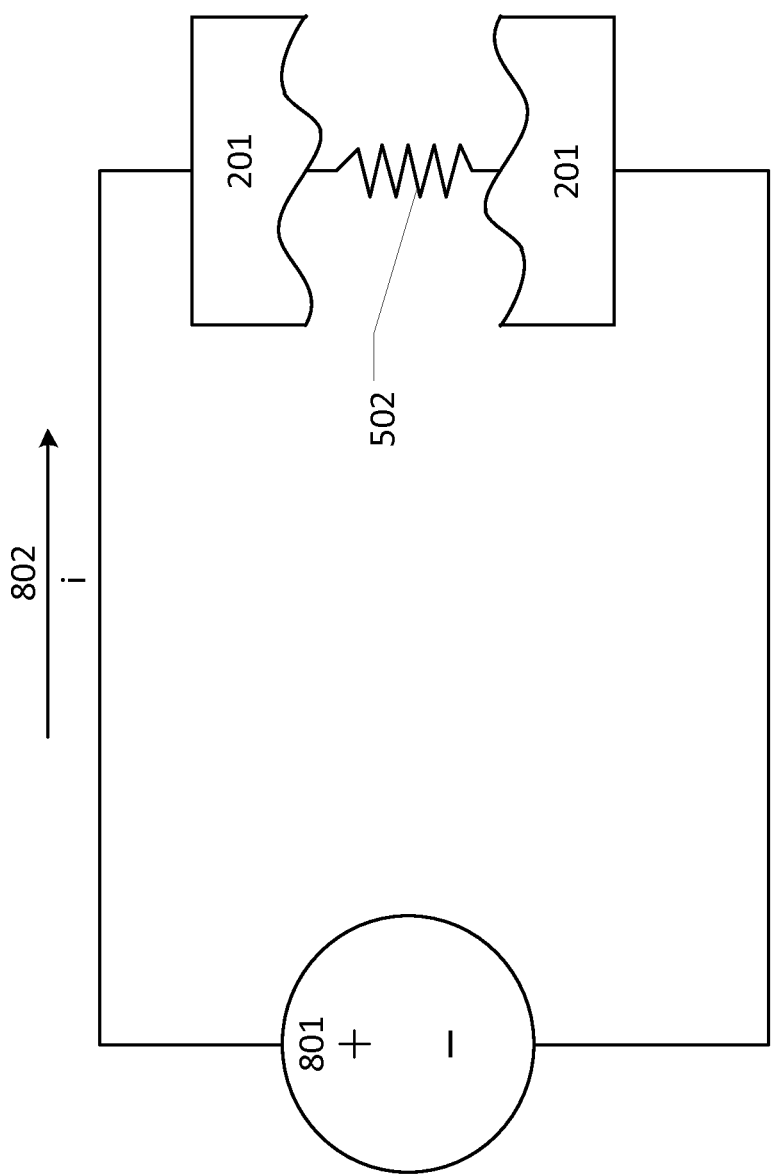
FIG. 8 illustrates a nanotechnology system for reading of DNA sequences through a nano-gap.

FIG. 8 illustrates a nanotechnology system for reading of DNA sequences through nano-gap 502. The resistive reader system can comprise nano-gap 502 between graphene 201 that connected to a voltage source 801. Using nano-gap sequencing, nano-gap 502 can initially be immersed in a conducting fluid and a potential voltage can be applied across nano-gap 502, due to conductions of ions through nano-gap 502 an electric current 802 can be observed. The amount of current 802 can be sensitive to the size and shape of nano-gap 502. As such, by being able to manipulate and stabilize substrate 101, a desired width on nano-gap 502 can be obtained, and readings made on resistive reader system can have high accuracy and resolution.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method for developing a nano-gap comprising
depositing a brittle material on a substrate;
depositing a conductive graphene layer at the surface of said brittle material;
placing one or more indentions on said brittle material to mark one or more positions on a single crack to be formed;
propagating a single crack through said brittle material and said graphene using a force, said crack 400 nanometers or less, a first side of said crack having a first height C1, and a second side of said crack having a second height C2; and
bending at said crack on said first side at an angle $l_1$ to reduce said crack by a first distance, and on said second side at an angle $l_2$, to reduce said crack by a second distance, to form a nanogap, said first distance equal to C1 $\cos(l_1)$, said second distance equal to C2 $\cos(l_2)$, said bending occurring only at said single crack.

2. The method of claim 1 wherein said one or more positions are one more end points.

3. The method of claim 2 wherein prior to placing said indentions on said brittle material comprises a step of mounting said substrate into a vacuum chamber of a microscope, and said indentions are placed using a scratching technique with said microscope.

4. The method of claim 3 wherein said microscope is an atomic force microscope (AFM).

5. The method of claim 3 wherein said microscope is a scanning electron microscope (SEM).

6. The method of claim 2 wherein said force is applied by bending said substrate around a bar.

7. The method of claim 1 wherein said nano-gap is reduced to less than 10 nanometers by said bending.

8. The method of claim 1 wherein after depositing said brittle material on said substrate comprises the step of measuring the thickness of said brittle material and said substrate.

9. The method of claim 1 wherein said force is compression force.

10. The method of claim 1 wherein said force is tensional force.

11. The method of claim 1 wherein said force is applied by bending said substrate around a bar.

12. The method of claim 1 wherein said substrate can comprise of a Poly-ethylene Terephthalate (PET).

13. The method of claim 1 wherein said brittle material comprises a salt.

14. The method of claim 1 wherein said brittle material comprises ceramic.

15. The method of claim 1 wherein said brittle material comprises silica glass substance.

16. The method of claim 1 wherein said conductive graphene layer is 2-dimensional (2D).

17. The method of claim 1 wherein said brittle film comprises a spin on glass (SOG) cured liquid glass.

18. The method of claim 1 further comprising the step of immersing said nano-gap in a conducting fluid;
electrically connecting a first portion of said graphene layer on a first side of said single crack to a first node in a circuit;
electrically connecting a second portion of said graphene layer on a second side of said single crack to a second node in said circuit, said first portion of said graphene layer and said second portion of said graphene layer electrically disconnected by said single crack; and
applying a voltage across said nano-gap.

19. The method of claim 18 further comprising the step of resistively reading a DNA sequence using said circuit.

* * * * *